(12) United States Patent
Sampson

(10) Patent No.: US 10,350,038 B1
(45) Date of Patent: Jul. 16, 2019

(54) DENTAL ARTICULATOR SYSTEM AND APPARATUS

(71) Applicant: Austin H. Sampson, Clearwater, FL (US)

(72) Inventor: Austin H. Sampson, Clearwater, FL (US)

( * ) Notice: Subject to any disclaimer, the term of this patent is extended or adjusted under 35 U.S.C. 154(b) by 0 days.

(21) Appl. No.: 15/803,817

(22) Filed: Nov. 5, 2017

Related U.S. Application Data

(60) Provisional application No. 62/539,301, filed on Jul. 31, 2017.

(51) Int. Cl.
| | | |
|---|---|---|
| *A62C 11/00* | (2006.01) | |
| *A61C 11/08* | (2006.01) | |
| *A61C 9/00* | (2006.01) | |
| *A61C 11/00* | (2006.01) | |

(52) U.S. Cl.
CPC .............. *A61C 11/082* (2013.01); *A61C 9/00* (2013.01); *A61C 11/003* (2013.01)

(58) Field of Classification Search
CPC ....... A61C 11/00; A61C 11/005; A61C 11/06; A61C 11/006
See application file for complete search history.

(56) References Cited

U.S. PATENT DOCUMENTS

| | | | | | |
|---|---|---|---|---|---|
| 1,050,933 | A | * | 1/1913 | Evans | ............ A61C 11/06 433/55 |
| 1,271,161 | A | * | 7/1918 | Hall | ............ A61C 11/06 433/59 |
| 1,636,321 | A | * | 7/1927 | Needles | ............ A61C 11/022 433/52 |
| 2,716,815 | A | * | 9/1955 | Ford | ............ A61C 11/022 433/196 |

(Continued)

OTHER PUBLICATIONS

Dawson, Peter E., "Functional Occlusion: From TMJ to Smile Design", Published by Mosby Inc., St. Louis, Missouri, Chapter 11 (Recording Centric Relation), pp. 91-101 (2007).

(Continued)

*Primary Examiner* — Ralph A Lewis
(74) *Attorney, Agent, or Firm* — The Law Office of Patrick F. O'Reilly III, LLC

(57) ABSTRACT

Dental articulator systems and dental articulators are disclosed herein. The disclosed dental articulator systems comprise a bite registrator, a dental articulator and a mounting jig. The bite registrator comprises a buccal rail configured to be positioned along the exterior perimeter of a patient's dentition; at least one vestibular component supported by and slidable along the buccal rail for identifying a reference position; and at least one bite registration module supported by and slidable along the buccal rail, and forming an aperture through which bite registration material may be injected into the patient's dentition. The dental articulator (Continued)

comprises an upper articulator member for mounting a maxillary dentition model, and a lower articulator member for mounting a mandibular dentition model. The mounting jig is configured to receive the bite registrator and indicate proper alignment of the position the maxillary dentition model and the mandibular dentition model with respect to one another.

17 Claims, 10 Drawing Sheets

(56) References Cited

U.S. PATENT DOCUMENTS

| | | | | |
|---|---|---|---|---|
| 4,600,386 | A * | 7/1986 | Feinmann | A61C 9/00 433/54 |
| 4,668,189 | A * | 5/1987 | Levandoski | A61C 11/00 433/55 |
| 4,762,490 | A * | 8/1988 | Ludwigs | A61C 11/006 433/55 |
| 4,773,854 | A * | 9/1988 | Weber | A61C 11/022 433/57 |
| 4,875,857 | A * | 10/1989 | Kubein-Messenburg | A61C 11/00 433/56 |
| 5,281,135 | A * | 1/1994 | Schwestka-Polly | A61C 11/00 433/215 |
| 9,089,384 | B1 | 7/2015 | Sampson | |
| 2014/0017627 | A1 * | 1/2014 | Fang | A61C 11/00 433/64 |
| 2016/0089219 | A1 * | 3/2016 | Kim | A61C 11/003 433/55 |

OTHER PUBLICATIONS

Monson, George S., "Original Communications: Applied Mechanics to the Theory of Mandibular Movements", The Dental Cosmos, vol. 74, No. 11, pp. 1039-1053 (Nov. 1932).

Prothero, James H., "Prosthetic Dentistry", Medico-Dental Publishing Co., Chicago, Illinois, Chapter 18 (Construction of Full Dentures), pp. 304-351 (1916).

Stuart, Charles E., "Articulation of Human Teeth", A Research Report by McCollum and Stuart, pp. 91-123 (1955).

* cited by examiner

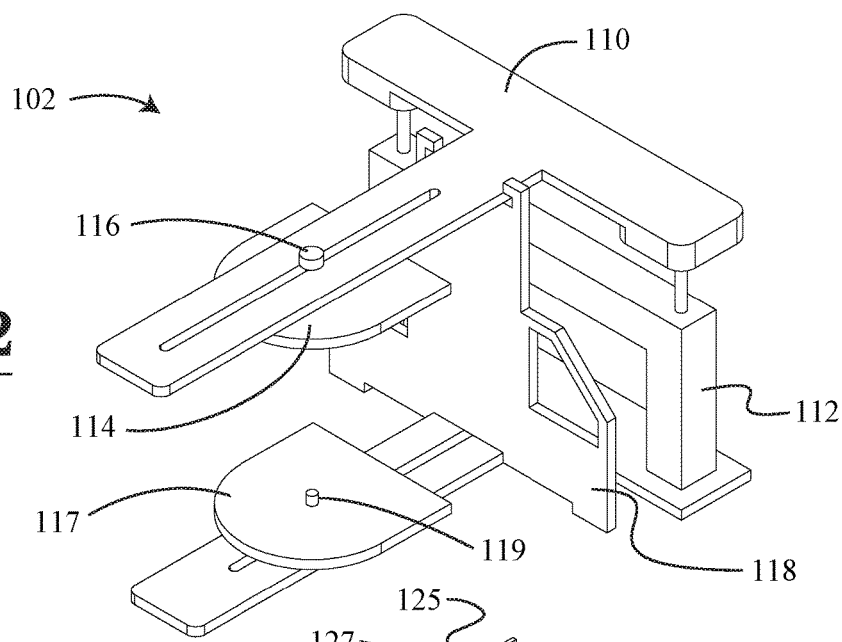
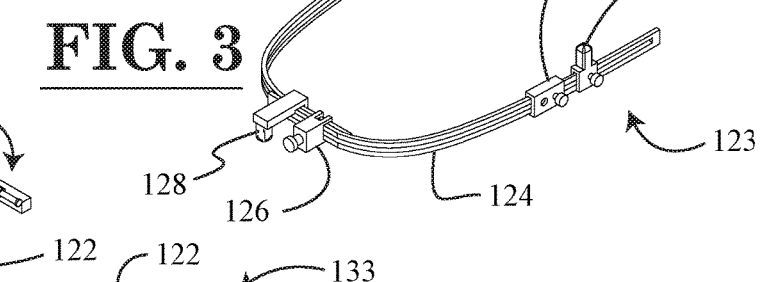
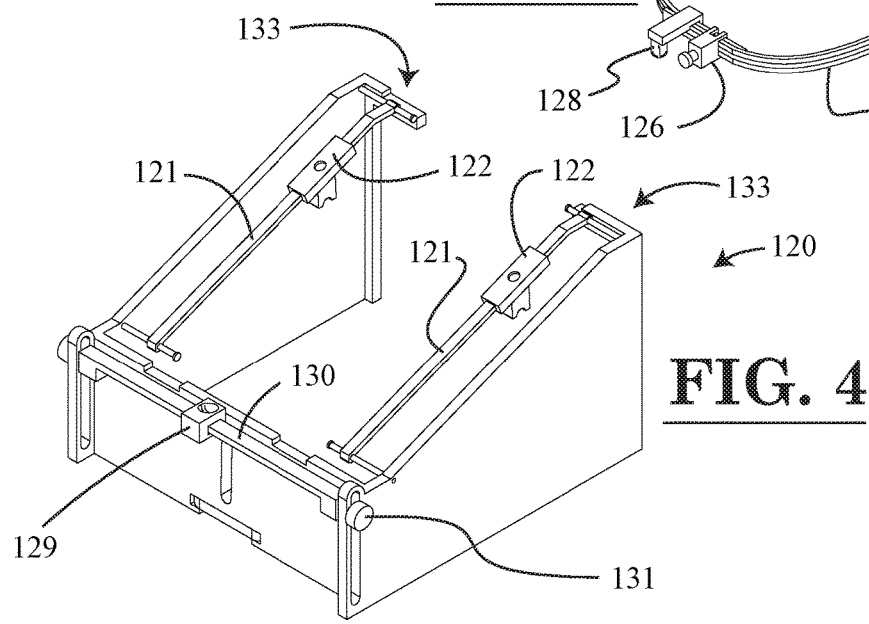

Detail "A"

DENTAL ARTICULATOR SYSTEM AND APPARATUS

CROSS-REFERENCE TO RELATED APPLICATIONS

This patent application claims priority to, and incorporates by reference in its entirety, U.S. Provisional Patent Application No. 62/539,301, entitled "Dental Articulator System And Apparatus", filed on Jul. 31, 2017.

STATEMENT REGARDING FEDERALLY SPONSORED RESEARCH OR DEVELOPMENT

Not Applicable.

NAMES OF THE PARTIES TO A JOINT RESEARCH AGREEMENT

Not Applicable.

INCORPORATION BY REFERENCE OF MATERIAL SUBMITTED ON A COMPACT DISK

Not Applicable.

BACKGROUND OF THE INVENTION

Technical Field

The present invention generally relates to dental articulators and dental articulator systems. More particularly, the present invention relates to quasi-adjustable dental articulators and systems employing quasi-adjustable dental articulators that take bite registration along the external perimeter rather than the traditional method of taking it between the teeth.

Background and Description of Related Art

As part of the process of fabricating dental restorations, models are taken of a patient's dentition. These models are then typically mounted on a dental articulator. An articulator is a mechanical device used in dentistry to which casts of the maxillary (upper) and mandibular (lower) teeth are fixed, reproducing recorded positions of the mandible in relation to the maxilla. An articulator assists in the fabrication of removable prosthodontic appliances (dentures), fixed prosthodontic restorations (crowns, bridges, inlays and onlays) and orthodontic appliances. A dental articulator replicates movement of the human jaw and allows a laboratory technician to fabricate the restoration indirectly so that some of the work can be performed in the laboratory.

Prior art dental articulators are available in three basic types: non-adjustable, semi-adjustable, and fully adjustable. In general, a more adjustable articulator results in a more accurate restoration. Further, a more accurate restoration results in less time making adjustments in the mouth.

Generally, the more complex the articulating system, the more time is needed to set up the articulator for use. Part of set-up time is spent taking a bite registration. Bite registrations are presently taken between the teeth and serve to orient upper and lower models to one another. In order to limit expense and save time setting up the articulating system, the use of non-adjustable articulators has become the norm. Use of a non-adjustable articulator, however, produces restorations that are far less accurate than those produced on semi-adjustable or fully adjustable articulators. As a result, far more time is needed for making occlusal adjustments at the time of delivery.

In addition to the time spent taking bite registrations, time must also be spent transferring information from the patient to the articulator. With a non-adjustable articulator, an interarch bite registration is utilized. Semi-adjustable and fully adjustable articulators also utilize bite registration, but they go a step further with a facebow apparatus that orients the models to a reference point on the skull. This, however, is extremely time-consuming both at the dental chair as well as in the dental laboratory.

A need therefore exists for a dental articulator and dental articulator system that provides accurate and efficient transferrance of information from the patient to the model. A further need exists for a dental articulator system and apparatus that produces restorations with greater precision. Yet a further need exists for a dental articulator system and apparatus that reduces the need for adjustments.

SUMMARY OF EXAMPLE EMBODIMENTS

Accordingly, the present invention is directed to a dental articulator system and a dental articulator that substantially obviates one or more problems resulting from the limitations and deficiencies of the related art.

In accordance with one or more embodiments of the present invention, there is provided a dental articulator system comprising: (i) a bite registrator, (ii) a dental articulator, and (iii) a mounting jig configured to receive the bite registrator. The bite registrator includes a buccal rail configured to be positioned along the exterior perimeter of a patient's dentition, at least one vestibular component supported by and slidable along the buccal rail for identifying a position relative to a maxillary dentition model and a mandibular dentition model, and at least one bite registration module supported by and slidable along the buccal rail, the bite registration module forming an aperture through which bite registration material may be injected into the patient's dentition. The dental articulator includes an upper articulator member, the upper articulator member comprising an upper mounting plate for mounting a maxillary dentition model; and a lower articulator member, the lower articulator member comprising a lower mounting plate for mounting a mandibular dentition model. The mounting jig includes at least one rail, and at least one movable linear member supported by and slidable along the at least one rail, the at least one movable linear member for cooperating with the at least one vestibular component of the bite registrator to align the maxillary dentition model and the mandibular dentition model with respect to one another.

In accordance with one or more other embodiments of the present invention, there is provided a dental articulator that includes an upper articulator member, the upper articulator member comprising an upper mounting plate for mounting a maxillary dentition model; a lower articulator member, the lower articulator member comprising a lower mounting plate for mounting a mandibular dentition model; and a mounting jig, the mounting jig being configured to receive a bite registrator comprising at least one vestibular component for identifying a position relative to a maxillary dentition model and a mandibular dentition model, the mounting jig comprising at least one movable linear member for cooperating with the at least one vestibular component to align the maxillary dentition model and the mandibular dentition model with respect to one another.

In accordance with yet one or more other embodiments of the present invention, there is provided a bite registrator that includes a buccal rail configured to be positioned along the exterior perimeter of a patient's dentition; at least one vestibular component supported by and slidable along the buccal rail for identifying a position relative to a maxillary dentition model and a mandibular dentition model; and at least one bite registration module supported by and slidable along the buccal rail, the bite registration module forming an aperture through which bite registration material may be injected into the patient's dentition.

BRIEF DESCRIPTION OF THE DRAWINGS

The invention will now be described, by way of example, with reference to the accompanying drawings, which are incorporated in and constitute a part of the specification, in which:

FIG. 2 is a perspective view of the upper and lower articulator members of the first example dental articulator system.

FIG. 3 is a perspective view of the bite registrator of the first example dental articulator system.

FIG. 4 is a perspective view of the mounting jig of the first example dental articulator system.

DRAWING REFERENCE NUMERALS

Figure 1:
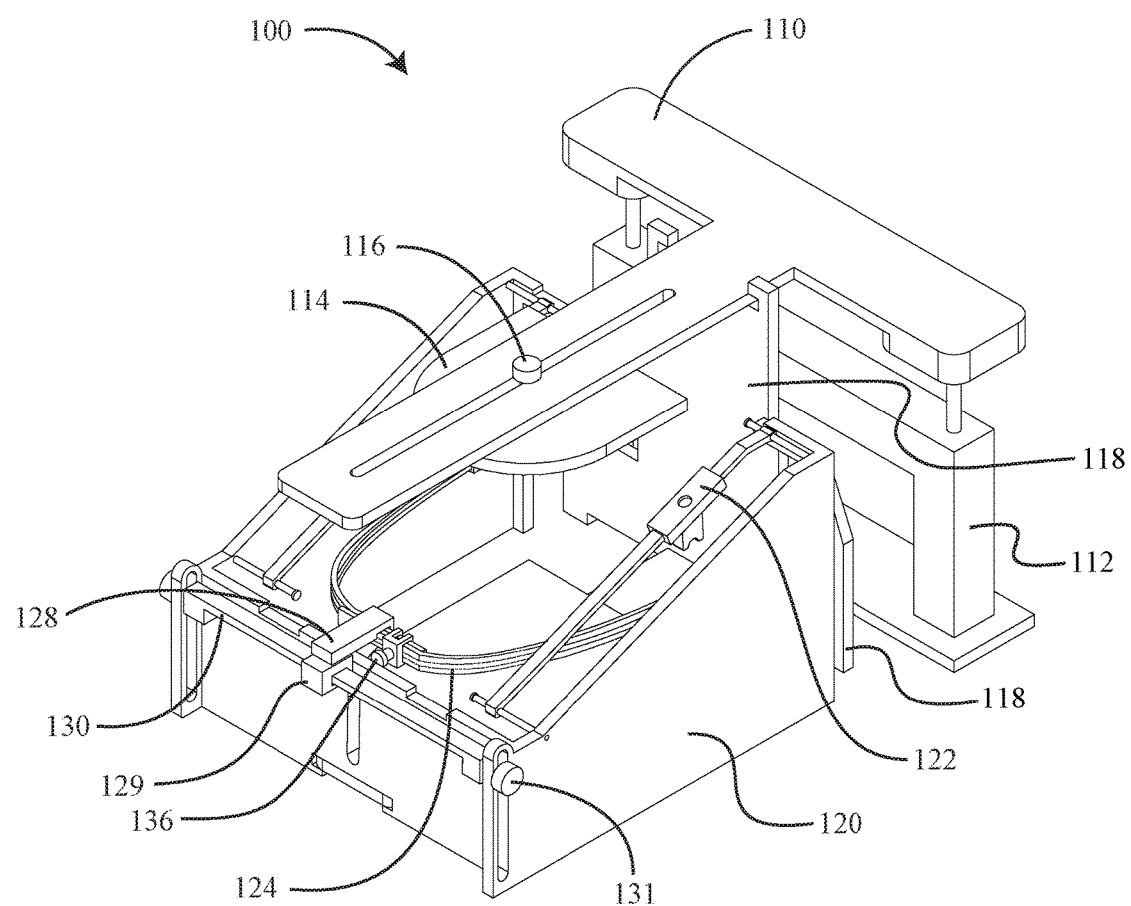
FIG. 1 is a perspective view of a first example dental articulator system.

The following reference characters identify the associated elements depicted in the drawings describing the present invention:

| | |
|---|---|
| 100 | Dental Articulator System |
| 102 | Dental Articulator |
| 110 | Upper Member of Articulator |
| 112 | Lower Member of Articulator |
| 114 | Upper Mounting Plate |
| 116 | Upper Adjustment Mechanism |
| 117 | Lower Mounting Plate |
| 118 | All-Purpose Mounting Plate |
| 119 | Lower Adjustment Mechanism |
| 120 | Mounting Jig |
| 121 | Posterior Rail |
| 122 | Posterior Linear Member |
| 123 | Bite Registrator |
| 124 | Band |
| 124a | First Portion of Band |
| 124b | Second Portion of Band |
| 125 | Posterior Vestibular Component |
| 126 | Bite Registrator Set Screw Adjustment Mechanism |
| 127 | Bite Registration Module |
| 128 | Anterior Vestibular Component |
| 129 | Anterior Linear Member |
| 130 | Anterior Rail |
| 131 | Anterior Adjustment Mechanism |
| 132 | Post of Articulator Lower Member |
| 133 | Posterior Adjustment Mechanism |
| 134 | Sacrificial Mounting Plate |
| 136 | Socket of Articulator Upper Member |
| 137 | Projections in Socket of Articulator Upper Member |
| 138 | Ball Member of Articulator Lower Member |
| 139 | Pins of Posterior Rail |
| 140 | Slot in Anterior Wall of Mounting Jig for Sacrificial Mounting Plate |
| 142 | Slot in Sidewall of Mounting Jig for Anterior Rail |
| 144 | Cap for Post of Sacrificial Mounting Plate |
| 146 | Fastener Member of Anterior Rail |
| 148 | Post of Sacrificial Mounting Plate |
| 150 | Spacer Member/Washer |
| 152 | Slot in Upper Member of Articulator |
| 154 | Aperture in Upper Mounting Plate |
| 156 | Slot in Lower Member of Articulator |
| 158 | Aperture in Lower Mounting Plate |
| 160 | Slot in Band of Bite Registrator |
| 162 | Set Screw of Bite Registrator Set Screw Adjustment Mechanism |
| 164 | Aperture of Bite Registration Module |
| 166 | Set Screw of Bite Registration Module |
| 168 | Set Screw of Posterior Vestibular Component |
| 170 | Negative Model of Patient's Bite Registration |
| 610 | Syringe |
| 1010 | Upper Dentition Model |
| 1110 | Lower Dentition Model |

DETAILED DESCRIPTION

To address the deficiencies of the prior art, the present application discloses a quasi-adjustable dental articulator and dental articulator system. The quasi-adjustable articulator of the present application represents a new category of dental articulator. In the disclosed articulator and system, the bite registration is taken along the external perimeter of the dentition rather than the traditional method of taking it between the teeth. The vestibular components substitute for the facebow apparatus, thereby transferring information from the patient more accurately and efficiently. Information gets to the laboratory technician more accurately without taking more time at the dental chair. Consequently, restorations can be produced with greater precision, and practitioners can save time in unnecessary adjustments.

In his textbook *Functional Occlusion*, Peter Dawson teaches the importance of centric relation. Defined as the rearmost, uppermost, midmost position of the condyle in the glenoid fossa, it is the well-documented starting point from which practitioners establish the accurate occlusion for patients. Existing bite registration systems utilize wax bite or silicone based registration materials, which by their very nature have a minimum thickness that separates the teeth, thereby pulling the condyles out of their ideal position. Consequently, models from such materials are mounted inaccurately, resulting in poor occlusion, centric prematurities, centric slides and lateral interferences.

The quasi-adjustable dental articulator and system address these problems by utilizing three unique components: an external bite registrator that accurately reproduces the relationship of the dentition to the condyles, a mounting jig that transfers information quickly and accurately to the articulator, and an articulator that eliminates the need for condylar settings and allows unrestricted reproduction of the patient's excursions. The interaction of the three components results in a unique and highly accurate dental articulator system. An overview of each component is set forth below:

Bite Registrator:

An exemplary bite registrator is comprised of the following parts:

(1) A horseshoe-shaped, rimmed band that can adjust to and accommodate various mouth sizes;

(2) At least one posterior vestibular component that slides along the bite registrator. In one embodiment, the bite registrator includes two posterior vestibular components, and the posterior vestibular components fit into the left and right upper buccal vestibular areas at approximately the second molar position.

(3) At least one centric bite module that slides along the bite registrator. In one embodiment, the bite registrator includes two such centric bite modules. Each centric bite module registers any two posterior teeth buccally with upper and lower teeth together.

(4) An anterior vestibular component that supports the anterior portion of the bite registrator. The anterior vestibular component slides along the bite registrator so as to fit into the anterior facial vestibular area.

(5) An anterior adjustment mechanism, such as a set screw, that adjusts the horizontal setting of the bite registrator.

The Quasi-Adjustable bite registrator solves the design flaws inherent in the prior art by:

(1) Taking a perimeter bite registration which does not change the position of the condyle. The registration is taken with the patient's teeth maximally intercuspated.

(2) Utilizing a self-enclosed centric bite module that can be injected into directly. The module presses the material against the teeth while the material sets.

(3) Accurately transferring occlusal information to the mounting jig and articulator without any distortion of the material.

It should be noted that in a recent study having 132 dentists take bite registrations most of whom were using some form of wax or silicon-based wafer in between the teeth, not one registration was shown to be accurate; therefore all of the cases were mounted incorrectly. Dawson further teaches that once the condyles are displaced from centric relation, disharmony between the occlusion and the TMJ is established.

Mounting Jig:

An exemplary mounting jig is comprised of the following parts:

(1) A framework that fits inside the perimeter of the articulator.

(2) An anterior wall whose height intersects a 10 centimeter (cm) line drawn from the center of the condyle.

(3) An all-purpose mounting plate that slides over the upper member of the articulator, rests on the ground and becomes a receptacle for the bite registrator.

(4) A vertically adjustable sacrificial mounting plate attached to the anterior wall of the mounting jig that can be raised or lowered and secured with a set screw.

(5) At least one posterior linear member. Each posterior linear member adjusts and provides a receptacle for a corresponding posterior vestibular component of the bite registrator.

(6) An anterior linear member that slides along a generally horizontal rail. The anterior linear member acts as a receptacle for the anterior vestibular component of the bite registrator.

(7) An anterior adjustment mechanism that allows vertical adjustment of the anterior rail so that the anterior linear member can be raised or lowered. The adjustment mechanism can be secured in place using, for example, a set screw.

In McCollum and Stuart's *Research Report* (1955), Charles Stuart notes that: "In order to develop the best form of treatment for mutilated mouths or to restore worn or decayed teeth, it is necessary to first make accurate models of the conditions. These models should be mounted on an instrument that actually reproduces the jaw motion. Again let me emphasize the necessity for having the models on the instrument to reproduce the relation of the teeth in the mouth to some plane in the face. Only by doing so is it possible to study the slant of the occlusal plane and the curve of Spee, in relation to the condyle path."

In *Prosthetic Dentistry* (1916), James Harrison Prothro further states that: "The average distance from the condylar centers to the mesioincisal angle of the lower incisor teeth is 4 inches or approximately 10 centimeters in a straight line. The second molars are situated practically halfway between the two points but being below a straight line, drawn between the two points mentioned, they are usually about 2¼ inches from the second molar position."

The mounting jig satisfies the requirements prescribed by Stuart and Prothro for accurately orienting the upper and lower model to the skull by:

(1) Utilizing the second molar area as a reference point in the skull that substitutes for the facebow apparatus.

(2) Providing the means to orient the models to the skull. Such means is completely lacking in a non-adjustable articulator.

(3) Providing a system that orients the model to the skull that is more efficient and less time-consuming than the facebow apparatus used in both semi-adjustable and fully adjustable articulators.

(4) Including an adjustable posterior and anterior linear member that adjusts to any length or width of dental arch while simultaneously transferring information to the articulator.

It should be noted that in the disclosed system, it is advisable to mount the lower dentition model first. By elevating the incisal edge of the anterior teeth on the lower dentition model to the level of the anterior wall of the mounting jig, the model is thus oriented accurately to the condyles. The bite registrator stabilizes the lower dentition model while stone is setting. The lower dentition model is further stabilized by the impression in the bite registration that is held in place by the all-purpose mounting plate in the back and the anterior linear member in the front.

Articulator:

An exemplary dental articulator is comprised of the following parts:

(1) An upper articulator module for mounting a maxillary dentition model; and (2) A lower articulator module for mounting a mandibular dentition model.

While no one can argue that the anatomy of the bony structures, muscles, and restricting ligaments influences the function of the teeth, from a strictly laboratory viewpoint in doing restorative dentistry, George Monson (*Dental Cosmos,* 1932) had a valid point. He stated: "Instead of studying the movements of the condyles independently to determine the relation of the two occluding surfaces of the teeth, we can, with check bites, go directly to the problem of occlusion. The movements of the condyles can be considered a result and not a guide. The guiding element within the mastication of food is the cusps of the teeth when the first contact is made with the opposing teeth, while the condyles guide the mandible to the first contact of the teeth, the major guidance is the teeth."

The quasi-adjustable articulator adheres to Monson's theory by:

(1) Avoiding the need for condylar settings that are time-consuming and unnecessary in most cases.

(2) Allowing the articulator to completely duplicate the patient's excursions without interferences.

(3) Demonstrating the patient's existing centric prematurities so that additional errors are not introduced into the system.

Accordingly, the Quasi-adjustable Articulating System not only accurately and efficiently replicates the true relationship of both the mandible to the maxilla and their relationship to the Temporomandibular Joint, but it also demonstrates accurate eccentric movement of the jaw. It is a revolutionary articulating system that provides an accurate representation of the patient's occlusion. It allows the practitioner to quickly and accurately take perimeter bite registrations with facebow accuracy without the time-consuming steps required to set up the apparatus. It enables the laboratory technician to quickly and accurately mount models so that they are true representations of the relationship of the models to the hinge axis, thereby satisfying any centric relation requirements. As a result, the Quasi-adjustable Articulating System allows the practitioner to avoid wasting valuable chair time on unnecessary occlusal adjustments.

Before more specifically describing the example dental articulator and dental articulator system, it is helpful to understand the example protocol for using the quasi-adjustable dental articulator system. The system is generally used in accordance with the following steps:

1. In the instance of crown and bridgework, the tooth is prepared and an impression is taken.

2. An impression is taken for an opposing dentition model. In particular, impressions of the upper and lower arches are taken.

3. The bite registrator is placed in the mouth with patient's teeth together. The sides of the bite registrator are closed against the teeth bilaterally and set screw is tightened. The horizontal (width) adjustment is set with the set screw so that the bite registration module is tight against the buccal (outside) contours of the teeth.

4. Both posterior vestibular components are set. The posterior vestibular components appear in the area between the teeth and the upper cheek (vestibular) area. They are set for the approximate area of the second molar even if it is not present.

5. The anterior vestibular component is set. The anterior vestibular component is adjusted to fit into the patient's anterior vestibular area, between the lower anterior teeth and the lower lip.

6. The bite registration modules are set. Each module slides around to find two posterior teeth together. The modules are placed against teeth bilaterally and tightened.

7. The bite registration material is injected into the bite registration module; the material is given a chance to harden.

8. Once the material is set, the set screw for the bite registrator is loosened and the apparatus is removed from the patient's mouth.

9. An all-purpose mounting plate is placed over the upper and lower arm members of the articulator at the front of the articulator, and then the all-purpose mounting plate is slid to the back of the articulator.

10. The mounting jig is placed around the upper and lower arm members of the articulator; the base slides over the lower arm member of the articulator.

11. The bite registrator is placed into the mounting jig. The arms of the registrator are placed into the openings of the all-purpose mounting plate. In one or more embodiments, the bite registrator may be placed into the mounting jig so that the front loop portion of the bite registrator fits into the two notches on the anterior wall of the mounting jig. The anterior vestibular component of the registrator rests on the anterior rail of the mounting jig which lines up therewith.

12. Each posterior linear member is lined up with a respective posterior vestibular component. Each posterior linear rail runs in a straight line from near the top of the anterior wall of the mounting jig to the center of the condyle on the lower member of the articulator. The rail will typically be approximately 10 cm in length, but it can be anywhere from 7-13 cm. Each posterior linear member is slidable to accommodate that distance. The male portion of each posterior vestibular component fits into the depression of the corresponding posterior linear member.

13. The anterior rail is elevated so that the sliding anterior linear member aligns with the anterior vestibular component and is secured in this position. The sliding anterior linear member is placed so that the depression on its surface receives the male portion of the anterior vestibular component. Note that the anterior vestibular component is located somewhat off the midline so as not to interfere with the set screw of the bite registrator.

14. The lower mounting plate of the articulator is then screwed into place.

15. The sacrificial mounting plate is then elevated so that the lower dentition model is vertically spaced apart from the lower mounting plate of the articulator. The sacrificial mounting plate is a disposable horseshoe-shaped component that supports the base of the model and can be adjusted vertically. The sacrificial mounting plate engages the lower model, and it is elevated so that the top of the incisal edge of the lower anterior teeth coincides with the top of the anterior wall of the mounting jig and approximately abuts the same. Mounting plaster is then mixed and placed in between the bottom of the model and the lower mounting plate of the articulator with the aforementioned sacrificial mounting plate in between. The mounting plaster is inserted through the waffle patterned openings of the sacrificial mounting plate. The outer surfaces of the posterior teeth will fit into the corresponding impression in the bite registration. That is, the sides or buccal surfaces of the teeth on the model should coincide with the corresponding depressions of the bite registration. Plaster is placed and allowed to harden. Once set, the protruding handle of the sacrificial mounting plate is eliminated.

16. The upper dentition model is placed in occlusion with the lower dentition model as dictated by the bite registrator. The upper dentition model rests on the lower dentition model.

17. Mounting plaster is then placed between the upper mounting plate of the articulator and the upper dentition model and allowed to harden.

18. Once all the mounting plaster is set, both mounting plates are removed from the articulator, the all-purpose mounting plate slides out, and is placed aside. Both of the mounting plates are then replaced with the teeth in their fully occluded position, and the case is ready for the construction of the restoration.

The disclosed dental articulator system, and parts thereof, will now be described by way of example, with reference to the accompanying drawings.

As shown in FIGS. 1-5, there is illustrated an example dental articulator system 100. Dental articulator system 100 generally includes three elements: a dental articulator 102, a bite registrator 123, and a mounting jig 120.

Figure 5:
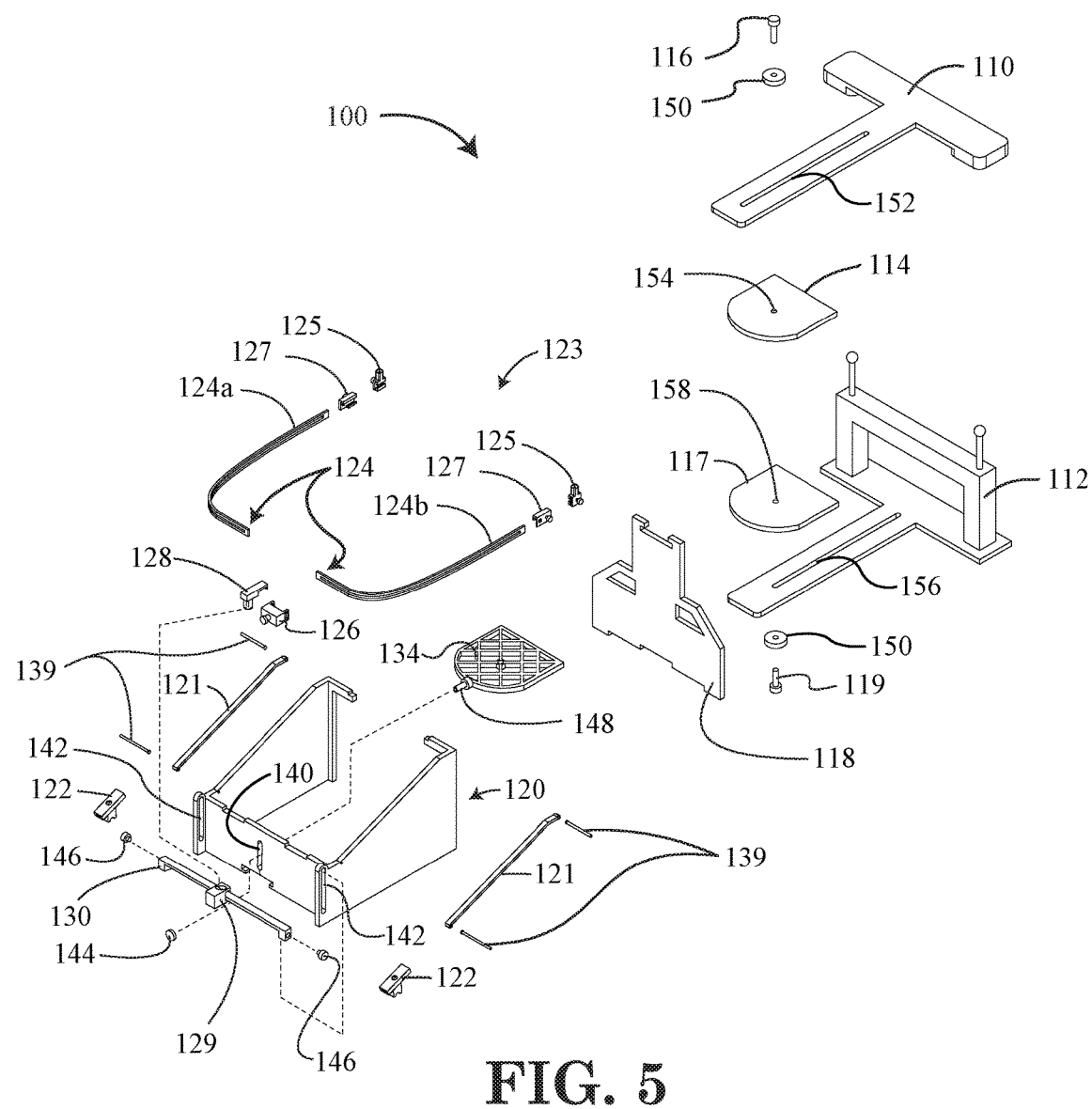
FIG. 5 is an exploded perspective view of the first example dental articulator system.

As best shown in FIGS. 1 and 2, the dental articulator 102 comprises an upper member 110 and a lower member 112. The upper member 110 supports an upper mounting plate 114 which is adjustably secured to the upper member 110 by upper adjustment mechanism 116. Similarly, the lower member 112 supports a lower mounting plate 117 which is adjustably secured to the lower member 112 by lower adjustment mechanism 119. In FIG. 5, it can be seen that the upper adjustment mechanism 116 may be in the form of a fastener that passes through the longitudinally-extending slot 152 in the upper member 110 and the circular aperture 154 in the upper mounting plate 114 so as to slidably couple the upper mounting plate 114 to the upper member 110 (i.e., the upper mounting plate 114 is slidably adjustable relative to the upper member 110 in an anterior-posterior direction). Similarly, it can be seen that the lower adjustment mechanism 119 also may be in the form of a fastener that passes through the longitudinally-extending slot 156 in the arm of the lower member 112 and the circular aperture 158 in the lower mounting plate 117 so as to slidably couple the lower mounting plate 117 to the arm of the lower member 112 (i.e., the lower mounting plate 117 is slidably adjustable relative to the arm of the lower member 112 in an anterior-posterior direction). Also, as shown in FIG. 5, each of the upper and lower mounting plates 114, 117 may be provided with a respective spacer member or washer 150 to form a gap between the upper and lower mounting plates 114, 117 and the respective upper and lower members 110, 112 on which they are supported.

Figure 7:
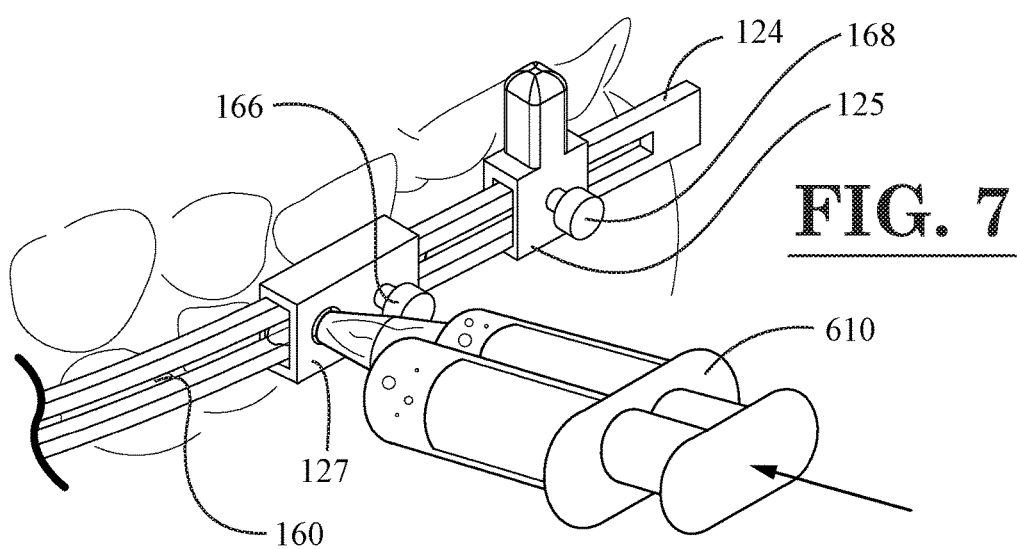
FIG. 7 is a magnified environmental view of the bite registrator of the first example dental articulator system.
Figure 8:
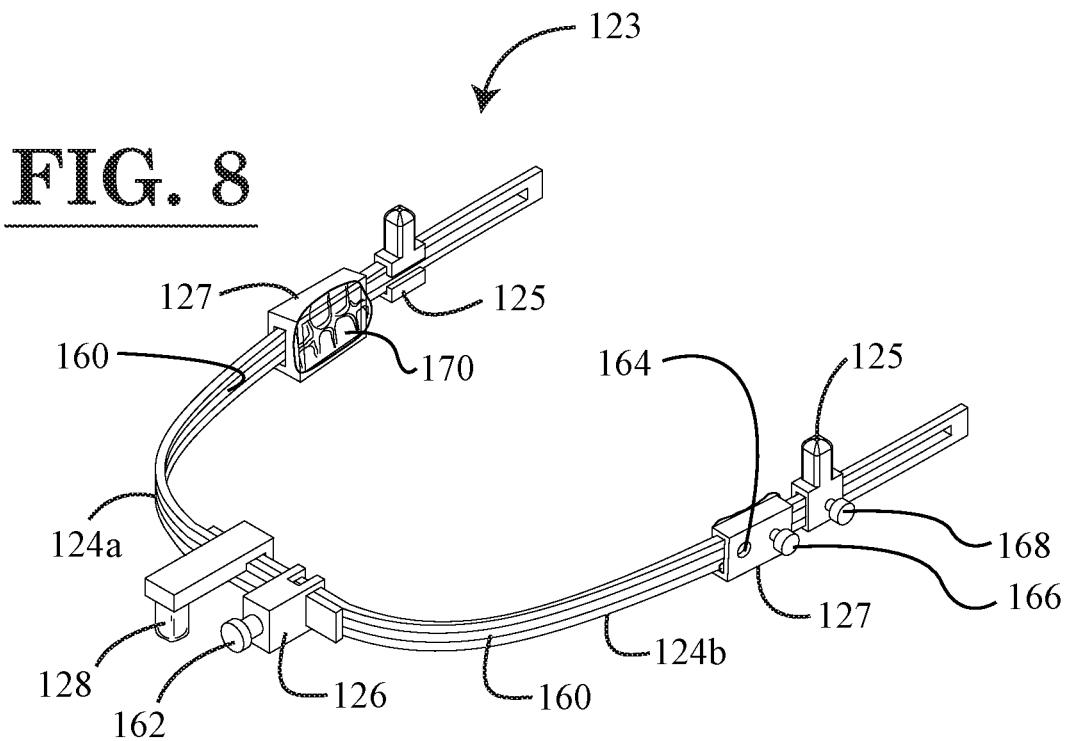
FIG. 8 is a magnified perspective view of the bite registrator of the first example dental articulator system.

As best shown in FIGS. 1 and 3, the bite registrator 123 comprises a horseshoe shaped band 124 (i.e., a buccal rail) with a central slot 160 formed therein. Band or rail 124 comprises a left and right portion 124b, 124a connected by bite registrator set screw adjustment mechanism 126 with set screw 162. The set screw 162 of the bite registrator set screw adjustment mechanism 126 allows the left and right portions 124b, 124a of band 124 to be adjusted to fit a patient's mouth, and secures the portions to maintain a customized size. Bite registrator 123 further comprises at least one posterior vestibular component 125 which slides along band 124 and fits into the left or right upper buccal vestibular areas at approximately the second molar position. Each posterior vestibular component 125 is provided with a set screw 168 that secures the posterior vestibular component 125 in place on the band 124 once the posterior vestibular component 125 has been moved to its desired position by a user (see FIGS. 6-8). Bite registrator 123 still further comprises at least one centric bite registration module 127 that slides along band 124 to register any two posterior teeth buccally with upper and lower teeth together. The centric bite registration module 127 is provided with a set screw 166 that secures the bite registration module 127 in place on the band 124 once the bite registration module 127 has been moved to its desired position by a user (see FIGS. 6-8). In addition, bite registrator 123 comprises an anterior vestibular component 128 that slides along band 124 and fits into the anterior facial vestibular area.

As best shown in FIGS. 1 and 4, the mounting jig 120 comprises an anterior rail 130 that supports anterior linear member 129. Anterior linear member 129 slides horizontally along anterior rail 130. An anterior adjustment mechanism 131 enables the anterior rail 130 and anterior linear member 129 to be adjusted vertically in order to enable the anterior linear member 129 to cooperate with the anterior vestibular component 128 when the bite registrator 123 is disposed within the mounting jig 120. More specifically, as shown in FIG. 5, the anterior rail 130 is provided with oppositely disposed fastener members 146 that slidingly couple the opposed ends of the anterior rail 130 to respective vertically-extending slots 142 in the oppositely disposed sidewalls of the mounting jig 120.

The mounting jig 120 further comprises a pair of posterior rails 121 that each supports a posterior linear member 122. Posterior linear member 122 slides horizontally along posterior rail 121. Each posterior rail 121 is supported from a respective sidewall of the mounting jig 120 by a pair of pins 139 (i.e., a pin 139 is provided at each of the opposed ends of each posterior rail 121 to support the posterior rail 121 from the respective sidewall of the mounting jig 120). A posterior adjustment mechanism 133 formed by the end portion of each posterior rail 121 and a respective one of the pins 139 enables each posterior rail 121 and posterior linear member 122 to be adjusted horizontally in a lateral direction (i.e., by sliding the posterior rail 121 on its pins 139) in order to enable each posterior linear member 122 to cooperate with a corresponding posterior vestibular component 125 when bite registrator 123 is disposed within the mounting jig 120.

FIG. 5 is an exploded perspective view of the first example dental articulator system 100. The components of the dental articulator, mounting jig, and bite registrator are shown exploded in FIG. 5 so that the details of these components may be better illustrated. In FIG. 5, it can be seen that the sacrificial mounting plate 134 is provided with a plurality of waffle patterned openings disposed therein so as to allow the mounting plaster to pass therethrough when the mounting plaster is placed between the lower dentition model 1110 and the lower mounting plate 117, as described above. The sacrificial mounting plate 134 is slidably attached to the anterior wall of the mounting jig 120 so that it is capable of being vertically adjusted. More specifically, the sacrificial mounting plate 134 is provided with a post 148 protruding from the front thereof that is slidingly received within the vertically-extending slot 140 in the anterior wall of the mounting jig 120 (see FIG. 5). A cap 144 is provided on the anterior end of the post 148 of the sacrificial mounting plate 134 so as to secure the post 148 within the slot 140. Also, it can be seen in FIG. 5 that the all-purpose mounting plate 118 is provided with top and bottom notches formed therein for receiving the respective top and bottom arms of the upper and lower articulator members 110 and 112. Also, the all-purpose mounting plate 118 is provided with two (2) spaced-apart apertures disposed in the approximate middle of the plate 118 for accommodating the opposed end portions of the horseshoe shaped band 124 of the bite registrator 123.

Figure 6:
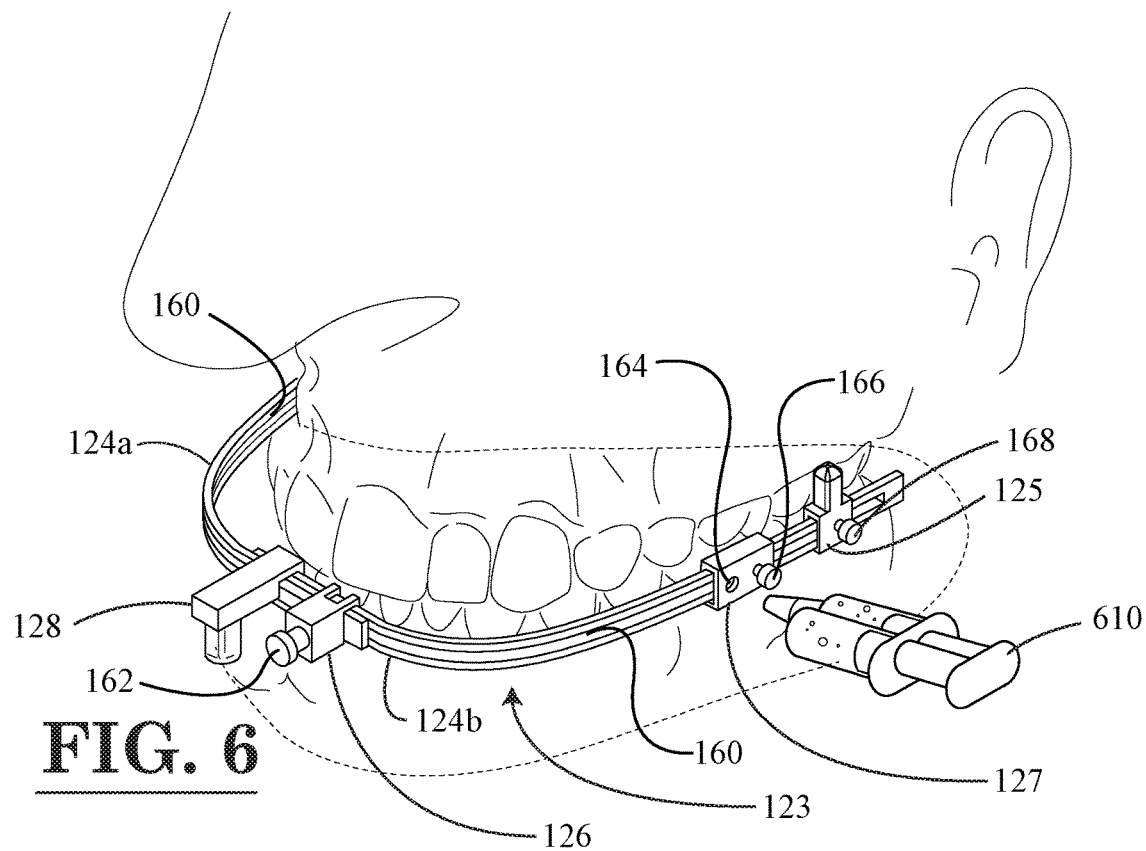
FIG. 6 is an environmental view of the bite registrator of the first example dental articulator system.

FIG. 6 is an environmental view of the bite registrator 123 of the first example dental articulator system 100. As shown, bite registrator 123 fits around the patient's mouth against the buccal contours of the patient's teeth. The two halves of band 124 of bite registrator 123 may be adjusted to fit the patient's mouth using the set screw 162 of the bite registrator set screw adjustment mechanism 126. Anterior vestibular component 128 is positioned to fit into the anterior facial vestibular area. Posterior vestibular components 125 are positioned to fit into the patient's vestibular area near the patient's second molar.

Figure 9:
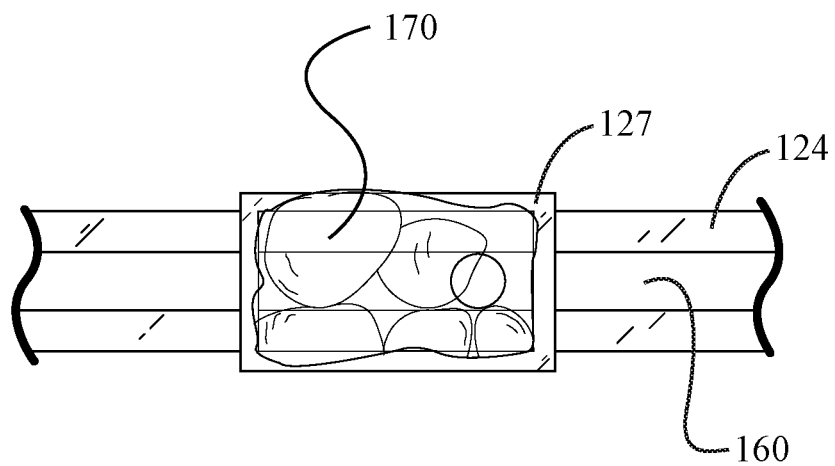
FIG. 9 is a magnified plan view of a portion of the bite registrator of the first example dental articulator system, which illustrates the rear of the bite registration module.

When the bite registrator 123 is properly positioned, the bite registration module 127 slides along band 124 generally along the point of contact between the patient's maxillary and mandibular dentition. As shown with more specificity in FIGS. 7-9, bite registration module 127 forms an aperture 164 through which bite registration material may be injected into the patient's mouth. Syringe 610 may be used to inject bite registration material at various points along band 124 through bite registration module 127 into the patient's mouth to form a negative model 170 of the patient's bite registration (i.e., the bite registration material is injected through the aperture 164 in the bite registration module 127, through the central slot 160 in the band 124, and onto the teeth of the patient to form the negative model 170).

Figure 10:
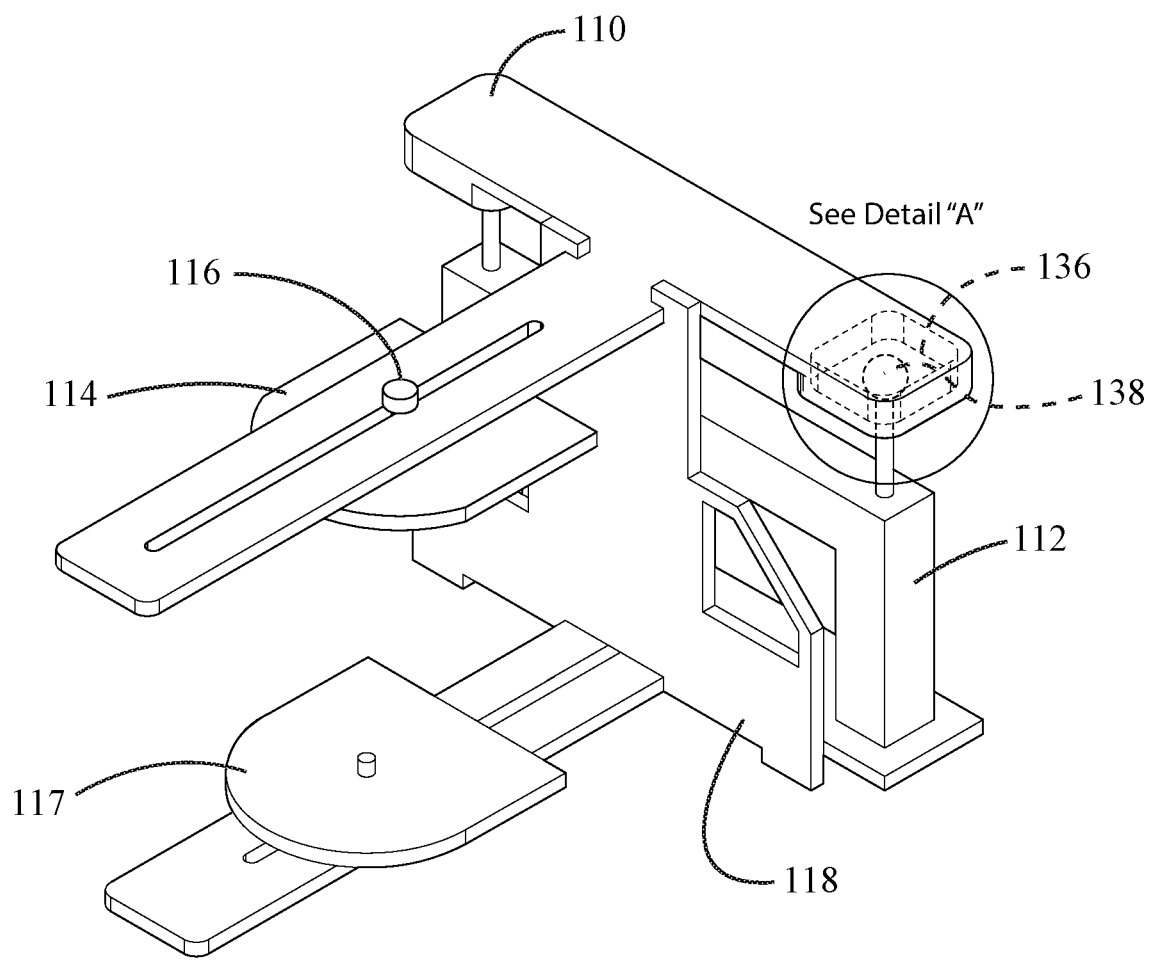
FIG. 10 is another perspective view of the upper and lower articulator members of the first example dental articulator system.
Figure 13:
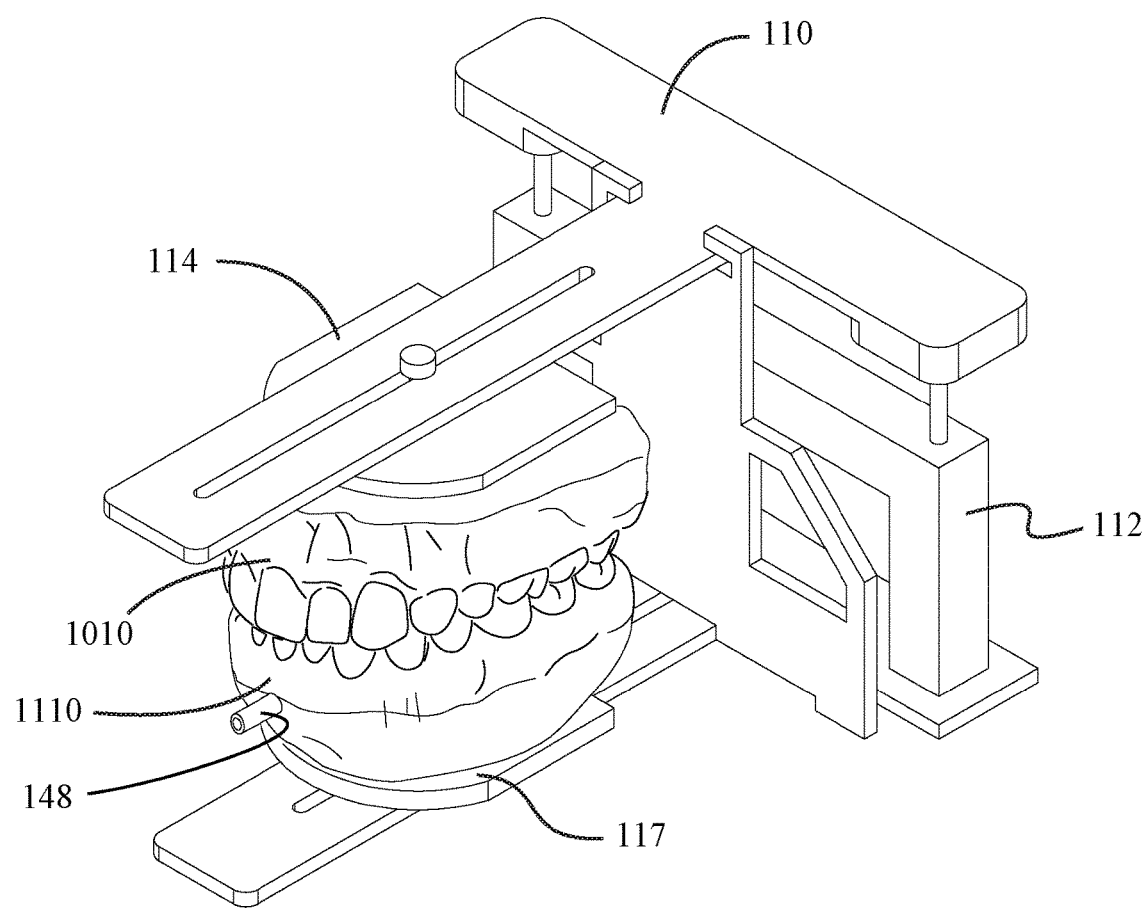
FIG. 13 is yet another perspective view of the upper and lower articulator members of the first example dental articulator system, wherein the upper and lower articulator members are supporting respective upper and lower dentition models.
Figure 14:
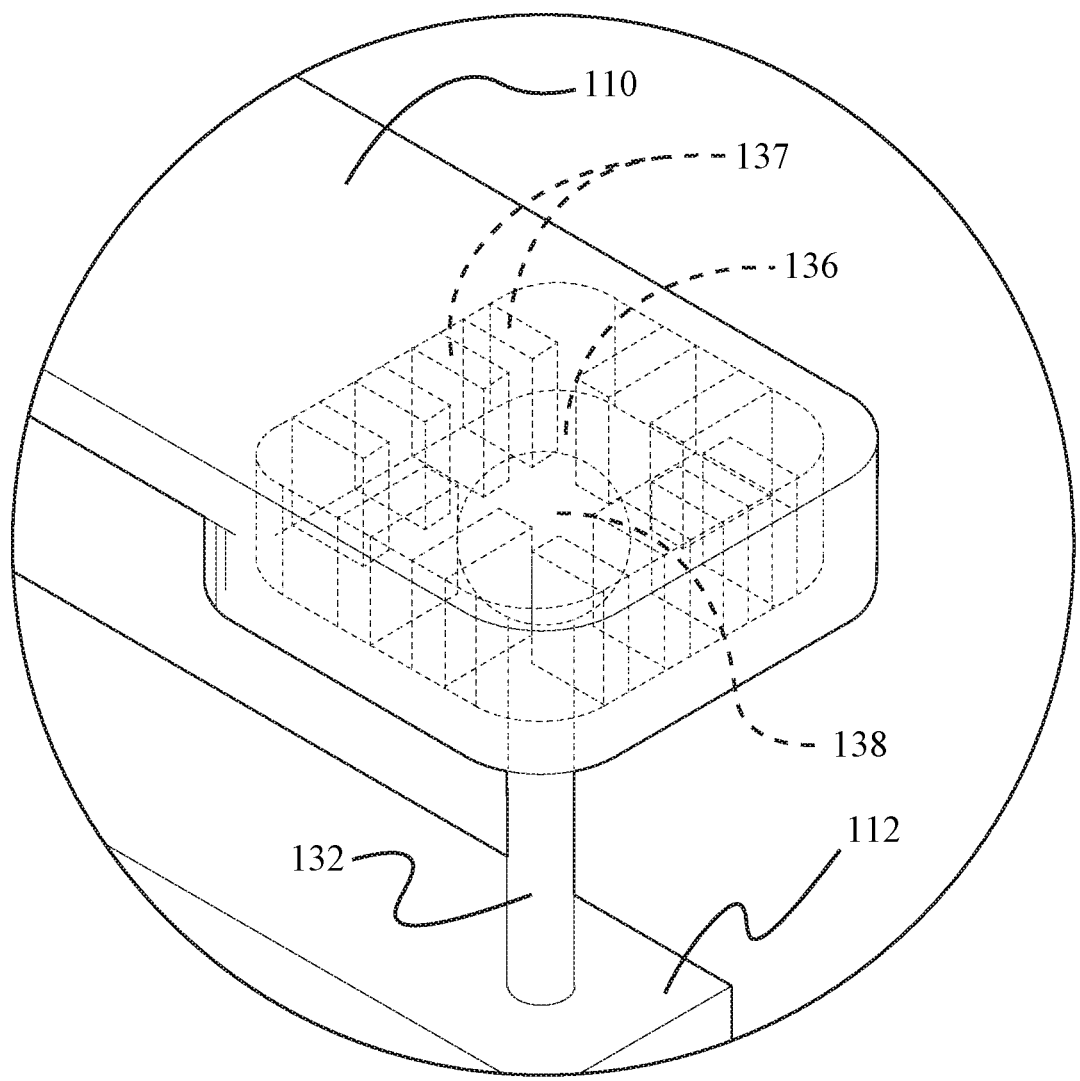
FIG. 14 is a magnified perspective view of Detail "A" of FIG. 10.

FIG. 10 is a perspective view of the upper and lower articulator members, 110 and 112, of the first example dental articulator system 100. As illustrated in FIG. 13, maxillary dentition 1010 is mounted on the upper articulator member 110 using the upper mounting plate 114. FIG. 10 further illustrates the ball and socket type connection between upper articulator member 110 and lower articulator member 112 at Detail "A." Detail "A" is illustrated with more particularity in FIG. 14, which depicts one of the ball and socket joints of the articulator in more detail. As shown in the detail view of FIG. 14, the ball member 138 of the lower articulator member 112 is received within the socket 136 of the upper articulator member 110 so as to allow the upper articulator member 110 to be rotated relative to the lower articulator member 112 (i.e., the ball and socket joint of the articulator generally provides three degrees of freedom (3 DOF) of movement). In FIG. 14, it can be seen that the ball member 138 of the lower articulator member 112 is mounted at the top of a support post 132. The socket 136 of the upper articulator member 110 is provided with a plurality of projections 137 that engage the ball member 138 in a friction fit type engagement that allows the upper articulator member 110 to be rotated relative to the lower articulator member 112 when a force is applied thereto by a user.

Figure 11:
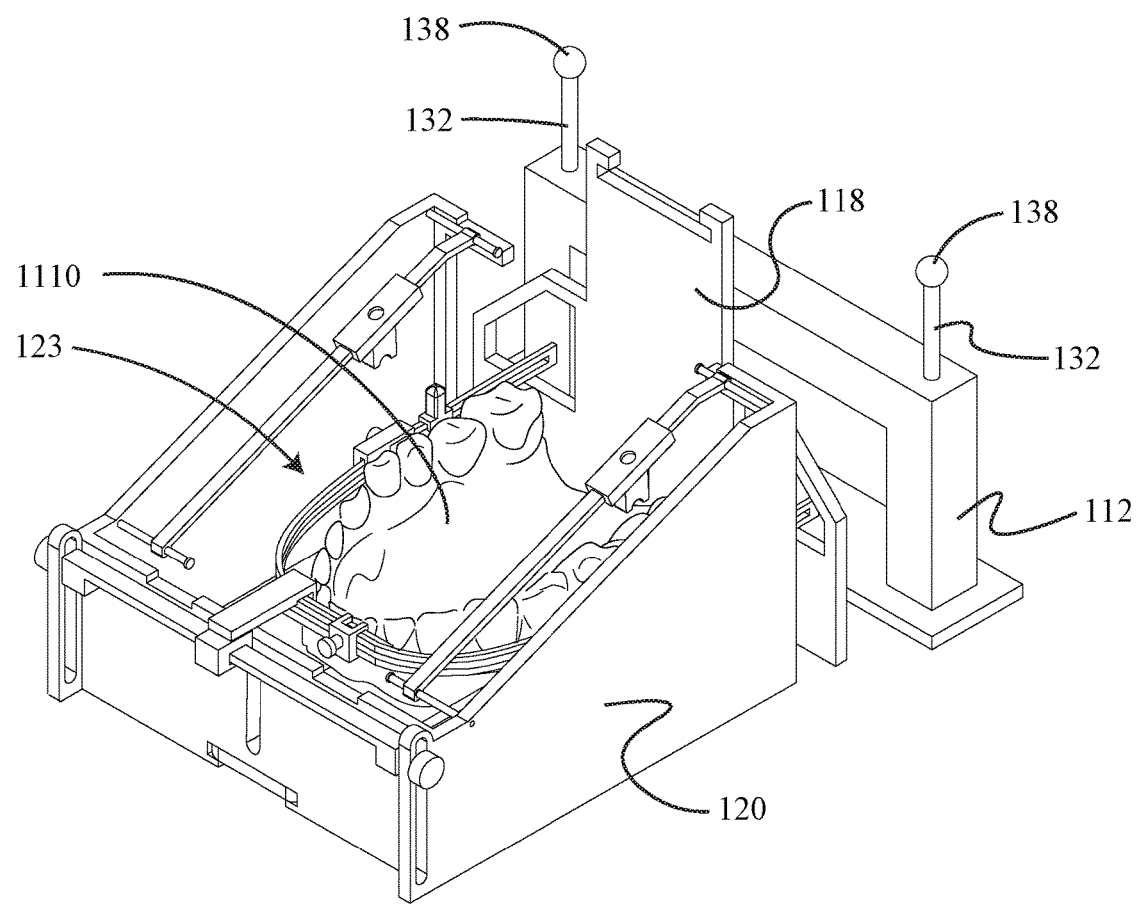
FIG. 11 is a perspective view of the lower articulator member, mounting jig and bite registrator unit of the first example dental articulator system.

FIG. 11 is a perspective view of the lower articulator member 112, mounting jig 120 and bite registrator 123 of the first example dental articulator system 100. As illustrated, the bite registrator 123 is disposed in cooperation with the mounting jig 120, and mandibular dentition 1110 is mounted on the lower articulator member 112 using the lower mounting plate 117.

Figure 12:
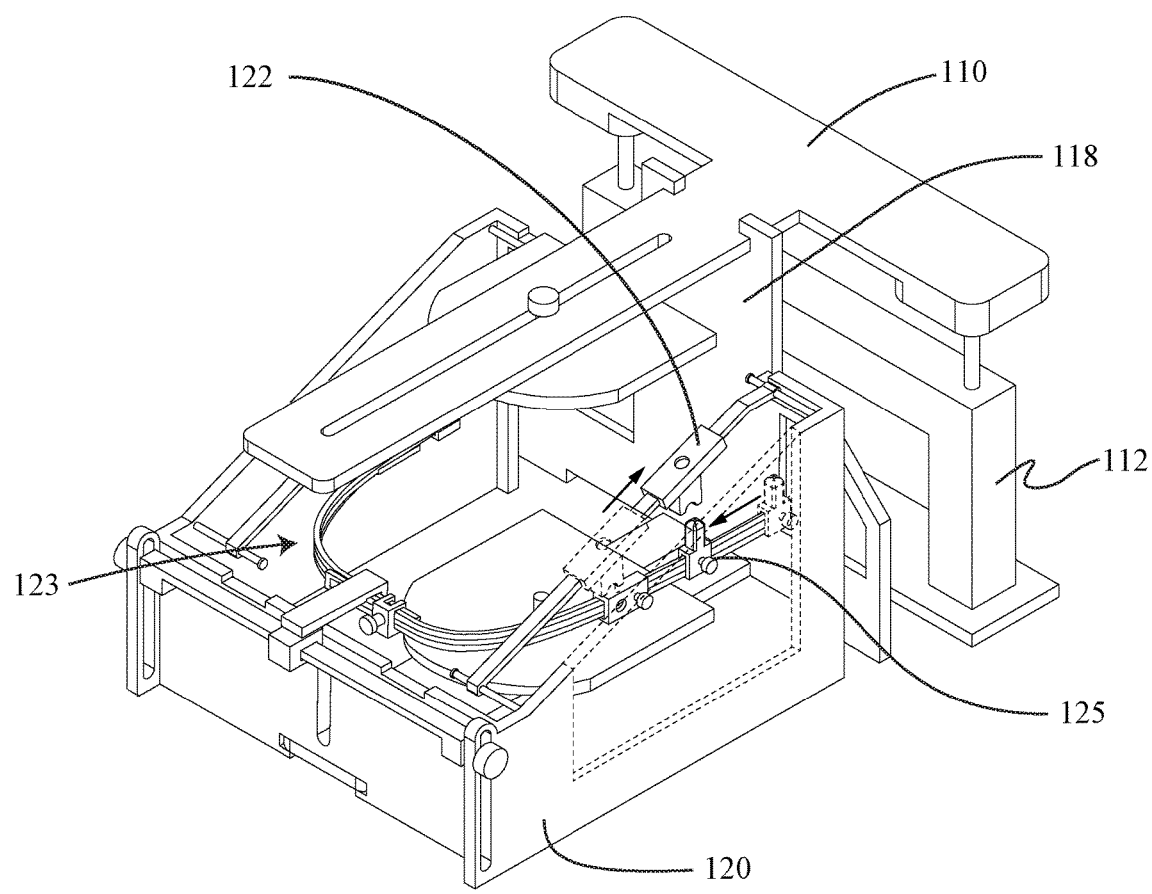
FIG. 12 is a cutaway perspective view of the first example dental articulator system.

FIG. 12 is a cutaway perspective view of the first example dental articulator system 100. In FIG. 12, a side wall of the mounting jig 120 is depicted with ghost lines, thereby illustrating the slidable positioning of posterior linear member 122 so as to align the posterior linear member 122 with the posterior vestibular component 125.

FIG. 13 is a perspective view of the upper and lower articulator members, 110 and 112, of the first example dental articulator system 100. As illustrated, maxillary dentition 1010 is mounted on the upper articulator member 110 using the upper mounting plate 114 and mandibular dentition 1110 is mounted on the lower articulator member 112 using the lower mounting plate 117.

While the devices, systems, methods, and so on have been illustrated by describing examples, and while the examples have been described in considerable detail, it is not the intention of the applicant to restrict, or in any way, limit the scope of the appended claims to such detail. It is, of course, not possible to describe every conceivable combination of components or methodologies for purposes of describing the devices, systems, methods, and so on provided herein. Additional advantages and modifications will readily appear to those skilled in the art. Therefore, the invention, in its broader aspects, is not limited to the specific details and illustrative examples shown and described. Accordingly, departures may be made from such details without departing from the spirit or scope of the applicant's general inventive concept. Thus, this application is intended to embrace alterations, modifications, and variations that fall within the scope of the appended claims. The preceding description is not meant to limit the scope of the invention. Rather, the scope of the invention is to be determined by the appended claims and their equivalents.

Finally, to the extent that the term "includes" or "including" is employed in the detailed description or the claims, it is intended to be inclusive in a manner similar to the term "comprising," as that term is interpreted when employed as a transitional word in a claim. Furthermore, to the extent that the term "or" is employed in the claims (e.g., A or B) it is intended to mean "A or B or both." When the applicants intend to indicate "only A or B, but not both," then the term "only A or B but not both" will be employed. Similarly, when the applicants intend to indicate "one and only one" of A, B, or C, the applicants will employ the phrase "one and only one." Thus, use of the term "or" herein is the inclusive, and not the exclusive use. See Bryan A. Garner, A Dictionary of Modern Legal Usage 624 (2d. Ed. 1995).

What is claimed is:

1. A dental articulator system comprising:
    a bite registrator, the bite registrator comprising:
        a buccal rail configured to be positioned along the exterior perimeter of a patient's dentition, the buccal rail of the bite registrator comprising a first rail portion and a second rail portion, at least one of the first and second rail portions of the buccal rail configured to be slidably adjustable relative to the other so as to allow the width of the bite registrator to be adjusted to fit a patient's mouth,
        at least one vestibular component supported by and slidable along the buccal rail for identifying a position relative to a maxillary dentition model and a mandibular dentition model, the at least one vestibular component comprising a body portion engaging the buccal rail and a protruding member extending outwardly from the body portion, the protruding member configured to fit into a vestibular area in the patient's mouth, and at least one bite registration module supported by and slidable along the buccal rail, the bite registration module comprising a module body portion engaging the buccal rail, and the module body portion forming an aperture through which bite registration material may be injected into the patient's dentition;

an upper articulator member, the upper articulator member comprising an upper mounting plate for mounting a maxillary dentition model;

a lower articulator member, the lower articulator member comprising a lower mounting plate for mounting a mandibular dentition model; and a mounting jig, the mounting jig being configured to receive the bite registrator, the mounting jig comprising:

at least one rail, and at least one movable linear member comprising a slidable carriage supported by and slidable along the at least one rail, the at least one movable linear member for cooperating with the at least one vestibular component to align the maxillary dentition model and the mandibular dentition model with respect to one another.

2. The dental articulator system of claim 1 wherein:

the at least one vestibular component of the bite registrator comprises:

an anterior vestibular component, a first posterior vestibular component, and a second posterior vestibular component;

the at least one rail of the mounting jig comprises:

an anterior rail positioned generally horizontally along the anterior of the mounting jig;

a first side rail positioned along a first side of the mounting jig, the first side rail running between the anterior and the posterior of the mounting jig, and a second side rail positioned along a second side of the mounting jig, the second side rail running between the anterior and the posterior of the mounting jig; and the at least one moveable linear member of the mounting jig comprises:

an anterior movable linear member supported by and slidable along the anterior rail, a first posterior movable linear member supported by and slidable along the first side rail, and a second posterior movable linear member supported by and slidable along the second side rail.

3. The dental articulator system of claim 2 wherein the mounting jig comprises an anterior adjustment mechanism enabling the anterior rail to be adjustably positionable along the vertical axis, the anterior adjustment mechanism comprising oppositely disposed fastener members that slidingly couple opposed ends of the anterior rail to respective vertically-extending slots in oppositely disposed sidewalls of the mounting jig.

4. The dental articulator system of claim 1 wherein the upper articulator member comprises an upper adjustment mechanism enabling the upper mounting plate to be adjustably positioned, the upper adjustment mechanism comprising a fastener that passes through a longitudinally-extending slot in an upper support of the upper articulator member and an aperture in the upper mounting plate so as to slidably couple the upper mounting plate to the upper support of the upper articulator member.

5. The dental articulator system of claim 1 wherein the lower articulator member comprises a lower adjustment mechanism enabling the lower mounting plate to be adjustably positioned, the lower adjustment mechanism comprising a fastener that passes through a longitudinally-extending slot in a lower support of the lower articulator member and an aperture in the lower mounting plate so as to slidably couple the lower mounting plate to the lower support of the lower articulator member.

6. The dental articulator system of claim 1 wherein the bite registrator further comprises a fastener securement mechanism configured to maintain the first and second rail portions in a fixed position relative to one another after the width of the bite registrator has been adjusted to fit the patient's mouth.

7. The dental articulator system of claim 6 wherein the fastener securement mechanism of the bite registrator comprises a set screw.

8. A dental articulator comprising:

an upper articulator member, the upper articulator member comprising an upper mounting plate for mounting a maxillary dentition model;

a lower articulator member, the lower articulator member comprising a lower mounting plate for mounting a mandibular dentition model; and a mounting jig, the mounting jig being configured to receive a bite registrator comprising at least one vestibular component for identifying a position relative to a maxillary dentition model and a mandibular dentition model, the mounting jig comprising at least one movable linear member for cooperating with the at least one vestibular component to align the maxillary dentition model and the mandibular dentition model with respect to one another;

the mounting jig further comprising:

an anterior rail positioned generally horizontally along the anterior of the mounting jig;

a first side rail positioned along a first side of the mounting jig, the first side rail running between the anterior and the posterior of the mounting jig, and a second side rail positioned along a second side of the mounting jig, the second side rail running between the anterior and the posterior of the mounting jig; and the at least one moveable linear member of the mounting jig comprising:

an anterior movable linear member comprising an anterior slidable carriage supported by and slidable along the anterior rail, a first posterior movable linear member comprising a first posterior slidable carriage supported by and slidable along the first side rail, and a second posterior movable linear member comprising a second posterior slidable carriage supported by and slidable along the second side rail.

9. The dental articulator of claim 8 wherein the at least one vestibular component of the bite registrator comprises an anterior vestibular component; and wherein the anterior movable linear member of the mounting jig is slidable along the anterior rail to a position cooperating with the anterior vestibular component of the bite registrator.

10. The dental articulator of claim 9 wherein the mounting jig comprises an anterior adjustment mechanism enabling the anterior rail to be adjustably positionable along the vertical axis, the anterior adjustment mechanism comprising oppositely disposed fastener members that slidingly couple opposed ends of the anterior rail to respective vertically-extending slots in oppositely disposed sidewalls of the mounting jig.

11. The dental articulator of claim 8 wherein the at least one vestibular component of the bite registrator comprises a first posterior vestibular component; and wherein the first posterior movable linear member of the mounting jig is slidable along the first side rail to a position cooperating with the first posterior vestibular component of the bite registrator.

12. The dental articulator of claim 8 wherein the upper articulator member comprises an upper adjustment mechanism enabling the upper mounting plate to be adjustably positioned, the upper adjustment mechanism comprising a fastener that passes through a longitudinally-extending slot in an upper support of the upper articulator member and an aperture in the upper mounting plate so as to slidably couple the upper mounting plate to the upper support of the upper articulator member.

13. The dental articulator of claim 8 wherein the lower articulator member comprises a lower adjustment mechanism enabling the lower mounting plate to be adjustably positioned, the lower adjustment mechanism comprising a fastener that passes through a longitudinally-extending slot in a lower support of the lower articulator member and an aperture in the lower mounting plate so as to slidably couple the lower mounting plate to the lower support of the lower articulator member.

14. A bite registrator comprising:

a buccal rail configured to be positioned along the exterior perimeter of a patient's dentition, the buccal rail comprising a first rail portion and a second rail portion, at least one of the first and second rail portions of the buccal rail configured to be slidably adjustable relative to the other so as to allow the width of the bite registrator to be adjusted to fit a patient's mouth;

at least one vestibular component supported by and slidable along the buccal rail for identifying a position relative to a maxillary dentition model and a mandibular dentition model, the at least one vestibular component comprising a body portion engaging the buccal rail and a protruding member extending outwardly from the body portion, the protruding member configured to fit into a vestibular area in the patient's mouth; and at least one bite registration module supported by and slidable along the buccal rail, the bite registration module comprising a module body portion engaging the buccal rail, and the module body portion forming an aperture through which bite registration material may be injected into the patient's dentition.

15. The bite registrator of claim 14 wherein the at least one vestibular component of the bite registrator comprises:

an anterior vestibular component configured to engage with an anterior movable linear member of a mounting jig;

a first posterior vestibular component configured to engage with a first posterior movable linear member of a mounting jig; and a second posterior vestibular component configured to engage with a second posterior movable linear member of a mounting jig.

16. The bite registrator of claim 14 further comprising:

a fastener securement mechanism configured to maintain the first and second rail portions in a fixed position relative to one another after the width of the bite registrator has been adjusted to fit the patient's mouth.

17. The bite registrator of claim 16 wherein the fastener securement mechanism comprises a set screw.

* * * * *